United States Patent
Feng et al.

(10) Patent No.: US 12,171,269 B2
(45) Date of Patent: Dec. 24, 2024

(54) ATOMIZER, ATOMIZATION SYSTEM AND OPERATION METHOD OF ATOMIZATION SYSTEM

(71) Applicant: LUXSHARE PRECISION INDUSTRY CO., LTD., Shenzhen (CN)

(72) Inventors: Yun Feng, Shenzhen (CN); Huabing Li, Shenzhen (CN); Yu Huang, Shenzhen (CN)

(73) Assignee: LUXSHARE PRECISION INDUSTRY CO., LTD., Shenzhen (CN)

( * ) Notice: Subject to any disclaimer, the term of this patent is extended or adjusted under 35 U.S.C. 154(b) by 398 days.

(21) Appl. No.: 17/572,244

(22) Filed: Jan. 10, 2022

(65) Prior Publication Data

US 2022/0295897 A1    Sep. 22, 2022

(30) Foreign Application Priority Data

Mar. 22, 2021  (CN) .......................... 202110302451.0

(51) Int. Cl.
*A24F 40/485*  (2020.01)
*A24F 40/10*   (2020.01)
(Continued)

(52) U.S. Cl.
CPC .......... *A24F 40/485* (2020.01); *A24F 40/10* (2020.01); *A24F 40/42* (2020.01); *A24F 40/46* (2020.01); *A24F 40/70* (2020.01); *A61M 11/042* (2014.02)

(58) Field of Classification Search
CPC ........ A24F 40/485; A24F 40/70; A24F 40/10; A24F 40/46; A24F 40/42; A61M 11/042
(Continued)

(56) References Cited

U.S. PATENT DOCUMENTS 10,285,449 B2 * 5/2019 Murison ............... A61M 11/042
2011/0005535 A1 * 1/2011 Xiu ......................... A24F 40/42
131/273
(Continued)

FOREIGN PATENT DOCUMENTS

CN   103932402 A    7/2014
CN   105078749 A   11/2015
(Continued)

OTHER PUBLICATIONS

Japanese Office Action for Japanese Application No. 2021-130051, dated May 30, 2023, with an English translation.

*Primary Examiner* — Gary F Paumen
(74) *Attorney, Agent, or Firm* — Birch, Stewart, Kolasch & Birch, LLP

(57) ABSTRACT

Disclosed are an atomizer, an atomization system and an operation method of the atomization system. The atomizer includes an atomization pipe, a reservoir and a flexible block piece. The atomization pipe includes an opening. The opening penetrates through an outer surface of the atomization pipe. The reservoir is disposed in the atomization pipe. The opening is communicated with the reservoir. The flexible block piece is disposed in the opening. The flexible block piece allows an injection needle to pass through the flexible block piece and enter the reservoir. The atomization system includes a base and the atomizer, and the atomizer is detachably connected to the base. The flexible block piece is filled in the opening to play a sealing role, and when specific liquid is consumed, the specific liquid can be injected into the reservoir by penetrating the injector into the flexible block piece, thus achieving reuse of the atomizer.

10 Claims, 3 Drawing Sheets

(51) Int. Cl.
  *A24F 40/42* (2020.01)
  *A24F 40/46* (2020.01)
  *A24F 40/70* (2020.01)
  *A61M 11/04* (2006.01)

(58) Field of Classification Search
  USPC .......................................................... 131/328
  See application file for complete search history.

(56) References Cited

U.S. PATENT DOCUMENTS

| | | | | |
|---|---|---|---|---|
| 2012/0167906 | A1* | 7/2012 | Gysland | A24F 40/00 |
| | | | | 131/328 |
| 2015/0305403 | A1* | 10/2015 | Coelho Belo Fernandes De Carvalho | F22B 1/284 |
| | | | | 131/328 |
| 2016/0192708 | A1* | 7/2016 | DeMeritt | H05B 3/40 |
| | | | | 392/390 |
| 2016/0227841 | A1 | 8/2016 | Li et al. | |
| 2016/0286860 | A1* | 10/2016 | Flayler | A61M 11/042 |
| 2017/0020195 | A1* | 1/2017 | Cameron | A24F 40/51 |
| 2017/0064997 | A1* | 3/2017 | Murison | A24F 40/53 |
| 2018/0125117 | A1* | 5/2018 | DeMeritt | A61M 15/002 |

FOREIGN PATENT DOCUMENTS

| | | |
|---|---|---|
| CN | 205695715 U | 11/2016 |
| CN | 206214421 U | 6/2017 |
| CN | 109480338 A | 3/2019 |
| CN | 110236228 A | 9/2019 |
| CN | 209749823 U | 12/2019 |
| CN | 110693715 A | 1/2020 |
| CN | 210248387 U | 4/2020 |
| CN | 111184266 A | 5/2020 |
| CN | 111232422 A | 6/2020 |
| CN | 211020984 U | 7/2020 |
| CN | 211407650 U | 9/2020 |
| CN | 211910536 U | 11/2020 |
| KR | 10-2013-0092251 A | 8/2013 |

* cited by examiner

ATOMIZER, ATOMIZATION SYSTEM AND OPERATION METHOD OF ATOMIZATION SYSTEM

CROSS-REFERENCE TO RELATED APPLICATION(S)

This application claims priority to Chinese Patent Application No. 202110302451.0 filed Mar. 22, 2021, the disclosure of which is incorporated herein by reference in its entirety.

TECHNICAL FIELD

The present disclosure belongs to the technical field of atomization systems and, specifically, relates to an atomizer, an atomization system and an operation method of the atomization system.

BACKGROUND

An electronic cigarette is an electronic product imitating a cigarette, with the same appearance, smoke, taste and feel as the cigarette. The electronic cigarette is a kind of atomizer driven by rechargeable lithium polymer battery, which can heat the smoke oil in the oil tank and turn nicotine into steam for users to smoke.

At present, atomizer, as a main component of the electronic cigarette, some atomizers can't fill cigarette oil repeatedly, so that the electronic cigarette can't be reused, and some atomizers are provided with oil filling holes, which can fill cigarette oil again, but it is easy to cause oil leakage, which often leads to scrapping and discarding atomizers, thereby not only increasing the consumption cost of users, but also easily causing waste of resources.

Therefore, there is an urgent need for an atomizer to solve the above technique problems.

SUMMARY

The object of the present disclosure is to provide an atomizer, an atomization system and an operation method of the atomization system, which can refill a specific liquid in the atomizer for repeated use, thereby reducing consumption costs and saving resources.

To achieve the object, the present disclosure adopts solutions described below.

Provided is an atomizer, including an atomization pipe, a reservoir and a flexible block piece.

The atomization pipe includes an opening, and the opening penetrates through an outer surface of the atomization pipe. The reservoir is disposed in the atomization pipe, and the opening is communicated with the reservoir. The flexible block piece is disposed in the opening and is configured to allow an injection needle to pass through the flexible block piece and enter the reservoir.

Optionally, the flexible block piece is made of a flexible plastic material or a flexible silica gel material.

Optionally, the atomizer further includes a fixing piece, where the fixing piece is sealed outside the opening and is attached to the flexible block piece, and the fixing piece is provided with a through hole.

Optionally, the atomizer further includes an atomization device, where the atomization device is disposed in the atomization pipe and is configured to generate heat.

Optionally, the atomizer further includes a conductive contact, where the conductive contact is electrically connected to the atomization device.

Optionally, the atomizer further includes a nozzle, where the nozzle is connected to one side of the atomization pipe, the atomization pipe further includes a through cavity, and the through cavity is communicated with the reservoir and the nozzle.

Optionally, the atomizer further includes an end cap, where the end cap covers the nozzle.

Optionally, the atomization pipe further includes a docking portion and a body, where the docking portion extends axially from the body and the docking portion is radially inward relative to the body, and the opening and the flexible block piece are located in the docking portion.

Provided is an atomization system, including a base and the above atomizer, where the atomizer is detachably connected to the base.

Optionally, the base includes a rod body, a coupling slot and a battery, where the coupling slot is located at one end of the rod body, the battery is disposed in the rod body, and one end of the atomization pipe provided with the flexible block piece is detachably coupled in the coupling slot.

Provided is an operation method of the atomization system, including the following steps.

The above atomization system is provided.

An injector containing a specific liquid is provided, where the injector includes an injection needle.

The injection needle is inserted into a flexible block piece of an atomizer and enters into a reservoir.

The specific liquid contained in the injector is injected into the reservoir.

The injector is separated.

The atomizer is connected to a base.

The atomization pipe atomizes the specific liquid in the reservoir.

The present disclosure has beneficial effects described below.

According to the atomizer and the atomization system provided by the present disclosure, the reservoir is used for storing the specific liquid, and the flexible block piece is filled in the opening to play a sealing role and prevent the specific liquid from flowing out through the opening; and when the specific liquid is consumed, the specific liquid can be injected into the interior of the reservoir by the injector penetrating into the flexible block piece, thus achieving reuse of the atomizer. The atomizer and the atomization system provided by the present disclosure can be used for many times, and waste caused by liquid leakage can be avoided, thereby reducing consumption costs and saving resources.

Figure 1:
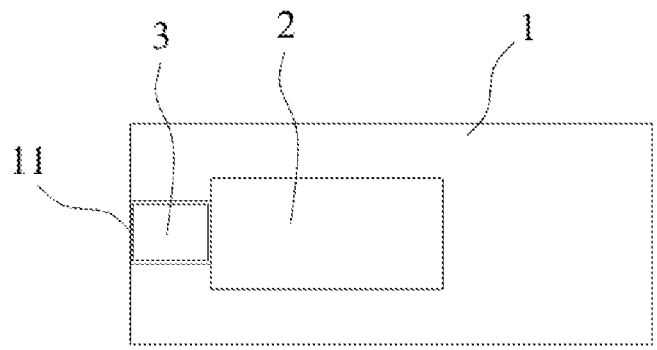
FIG. 1 is a schematic structure of an atomizer according to embodiment one of the present disclosure.

REFERENCE LIST 1 atomization pipe
2 reservoir
3 flexible block piece
4 conductive contact
5 atomization system
6 nozzle
7 end cap
10 base
11 opening
12 through cavity
13 body
14 docking portion
101 rod body
102 battery
103 coupling slot

DETAILED DESCRIPTION

Embodiments in accordance with the present disclosure will now be described in detail below. Examples of the embodiments are illustrated in the drawings, where the same or similar reference numerals indicate the same or similar elements or components having the same or similar functions. The embodiments described below with reference to the drawings are merely exemplary; they are intended to explain the present disclosure, and are not to be construed as limiting the present disclosure.

In the description of the present disclosure, unless otherwise expressly specified and limited, the term "connected to each other", "connected" or "installed" is to be construed in a broad sense, for example, as installed connected or detachably connected; mechanically connected or electrically connected; directly connected to each other or indirectly connected to each other via an intermediary; or internally connected between two elements or interactional relations between two elements. For those of ordinary skill in the art, specific meanings of the preceding terms in the present utility model may be understood based on specific situations.

In the description of the present disclosure, unless otherwise expressly specified and limited, when a first feature is described as "on" or "below" a second feature, the first feature and the second feature may be in direct contact or be in contact via another feature between the two features instead of being in direct contact. Moreover, when the first feature is described as "on", "above" or "over" the second feature, the first feature is right on, above or over the second feature or the first feature is obliquely on, above or over the second feature, or the first feature is simply at a higher level than the second feature. When the first feature is described as "under", "below" or "underneath" the second feature, the first feature is right under, below or underneath the second feature or the first feature is obliquely under, below or underneath the second feature, or the first feature is simply at a lower level than the second feature.

The solutions of the present disclosure will be further described below through specific embodiments in conjunction with the drawings.

Embodiment One

As shown in FIG. 1, an atomizer provided by the present embodiment includes an atomization pipe 1, a reservoir 2 and a flexible block piece 3. The atomization pipe 1 includes an opening 11, and the opening 11 penetrates through an outer surface of the atomization pipe 1. The reservoir 2 is disposed in the atomization pipe 1, and the opening 11 is communicated with the reservoir 2. The flexible block piece 3 is disposed in the opening 11 and is configured to allow an injection needle to pass through the flexible block piece 3 and enter the reservoir 2.

According to the atomizer provided by the present disclosure, the reservoir stores a specific liquid, and the flexible block piece 3 is filled in the opening 11 to play a sealing role and prevent the specific liquid from flowing out through the opening. When the specific liquid is consumed, the specific liquid can be injected into the interior of the reservoir 2 by the injection needle of the injector penetrating into the flexible block piece 3, thereby achieving reuse of the atomizer. Therefore, the atomizer provided by the present disclosure can be used for many times, and waste caused by liquid leakage is avoided, thereby reducing consumption costs and saving resources. In some embodiments, the specific liquid is, for example, but not limited to, cigarette oil or medicine. The atomizer should not be limited to the application of electronic cigarettes, but also can be used as medical atomization inhalers.

Embodiment Two

The present embodiment is further a limitation based on embodiment one.

The flexible block piece 3 is made of a flexible plastic material or a flexible silica gel material. The flexible block piece 3 can not only play a very good sealing role, but also can be penetrated by an injector, and does not leak after injection, and a specific liquid can be repeatedly injected. In the present embodiment, the flexible block piece 3 is made of a hospital-level flexible plastic material, similar to a medical infusion bottle stopper, and can be penetrated into an injection needle for many times without leaking liquid.

The atomizer provided by the present disclosure further includes a fixing piece, where the fixing piece is sealed outside the opening 11 and is attached to the flexible block piece 3, and the fixing piece is provided with a through hole. The fixing piece is sealed outside the opening 11, and is used for fixing the flexible block piece 3, so as to prevent an injection needle from moving the flexible block piece 3 when injecting the specific liquid, thereby affecting the sealing performance of the reservoir 2. The through hole in the fixing piece is used for the injection needle passing through, so that the injection needle can smoothly penetrate into the flexible block piece 3. Optionally, the fixing piece may be a mesh structure, and mesh holes on the fixing piece can allow the injection needle to pass through, The multiple injections are carried out through different mesh holes in sequence, so that leakage liquid caused by the injection needle penetrating into the same position for many time to enlarge the perforation of the flexible block piece 3 is avoided.

As shown in FIG. 2, the atomizer provided by the present disclosure further includes an atomization device 5, where the atomization device 5 is disposed in the atomization pipe 1 and is configured to generate heat. The atomization device 5 atomizes the specific liquid by generating heat. The atomization device 5 includes an atomization head, a heating coil and the like, and the specific structure of the atomization device 5 and working principle of the atomization device 5 may refer to the related art and will not be described here.

The atomizer provided by the present disclosure further a nozzle 6, where the nozzle 6 is connected to one side of the atomization pipe 1. The atomization pipe 1 further includes a through cavity 12, and the through cavity 12 is communicated with the reservoir 2 and the nozzle 6. Gas formed after atomizing the specific liquid is sucked out or discharged through the nozzle 6.

Figure 2:
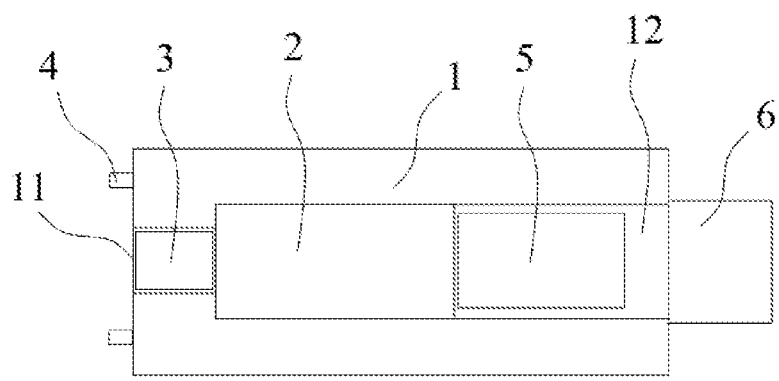
FIG. 2 is a schematic structure of an atomizer according to embodiment two of the present disclosure.
Figure 3:
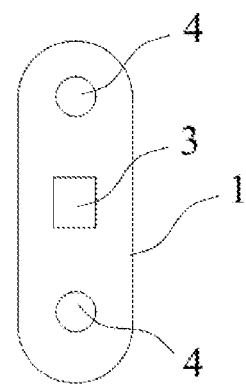
FIG. 3 is a left view of FIG. 2.

As shown in FIGS. 2 and 3, the atomizer provided by the present embodiment further includes a conductive contact 4, where the conductive contact 4 is electrically connected to the atomization device 5. The conductive contact 4 is used for energizing the atomization device 5. Specifically, both ends of the heating coil of the atomization device 5 are welded or soldered to two conductive contacts 4, respectively, and the two conductive contacts 4 can be connected to a positive electrode of the power supply and a negative electrode of the power supply, respectively. When the two conductive contacts 4 are connected to the power supply, the heating coil is energized to generate heat, thereby heating the specific liquid, evaporating the specific liquid to volatilize and atomize the specific liquid so as to form smoke.

Embodiment Three

The present embodiment is further a limitation based on embodiment two.

Figure 4:
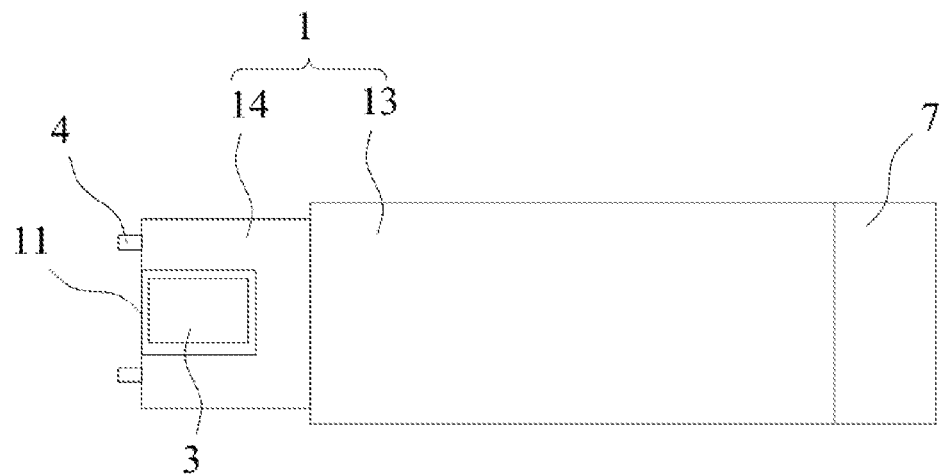
FIG. 4 is a schematic structure of an atomizer according to embodiment three of the present disclosure.

As shown in FIG. 4, in the present embodiment, the atomization pipe 1 further includes a docking portion 14 and a body 13, where the docking portion 14 extends axially from the body 13 and the docking portion 14 is radially inward relative to the body 13, and the opening 11 and the flexible block piece 3 are located in the docking portion 14.

The atomizer provided by the present embodiment further includes an end cap 7, and the end cap 7 covers the nozzle 6. The end cap 7 can prevent the nozzle 6 from being contaminated by foreign objects, and keep the nozzle 6 clean and sanitary. The end cap 7 and the nozzle 6 may be clamped or threaded, which not only ensures the firmness of the connection, but also facilitates disassembly.

Embodiment Four

Figure 5:
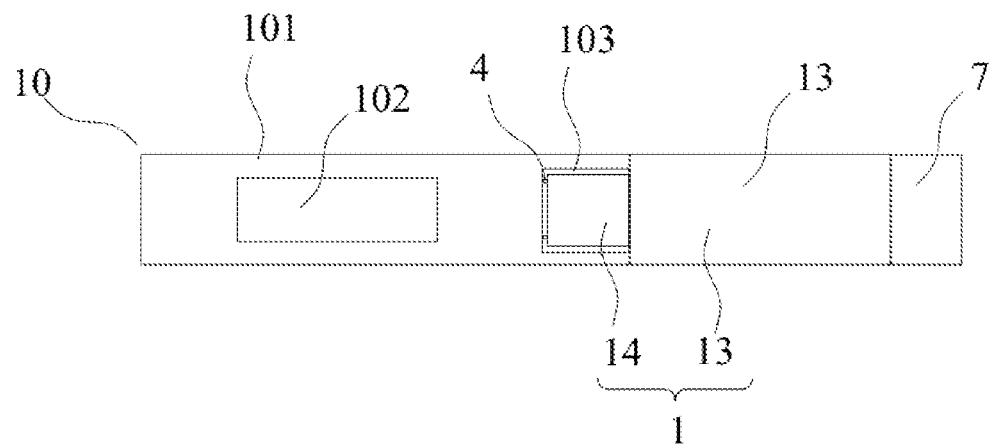
FIG. 5 is a schematic structure of an atomization system according to embodiment four of the present disclosure.

As shown in FIG. 5, an atomization system is provided in the present disclosure and includes an atomizer. The atomizer is, for example, but not limited to, the atomizer of embodiment three. The atomization system further includes a base 10, and the atomizer is detachably connected to the base 10.

Specifically, the base 10 includes a rod body 101, a coupling slot 103 and a battery 102. The coupling slot 103 is located at one end of the rod body 101, the battery 102 is disposed in the rod body 101, and one end of the atomization pipe 1 provided with the flexible block piece 3 is configured to be detachably coupled in the coupling slot 103. The rod body 101 is further provided with a control circuit, and the control circuit is electrically connected to the battery 102. When the docking portion 14 is coupled in the coupling slot 103, the conductive contacts 4 disposed on the docking portion 14 contacts the control circuit to achieve electrical connection, supply power to the heating coil, and achieve conductive atomization of the atomization system.

In use, the base 10 is connected to the atomizer to form the atomization system, and the flexible block piece 3 is located inside the atomization system. When the specific liquid needs to be injected, the atomizer is removed from the base 10 to expose the flexible block piece 3 so as to facilitate the injection of the specific liquid. In some embodiments, the flexible block piece 3 may also be disposed on an outer surface of the atomizer without contacting the base 10; in this manner, a user may inject the specific liquid into the reservoir 2 by inserting the injection needle into the flexible block piece 3 while the atomizer is still connected to the base 10. The atomization pipe 1 may be threaded to the rod body 101 by internal and external threads. In some embodiments, the atomization system is an electronic cigarette, the base 10 is a cigarette rod, and the atomizer is provided with a smoke bomb, and the reservoir 2 is used for storing smoke oil. In some embodiments, the atomization system is used for atomizing medicines, the base 10 is a control and power supply device and the reservoir 2 of the atomizer is used for storing medicines.

Embodiment Five

Figure 6:
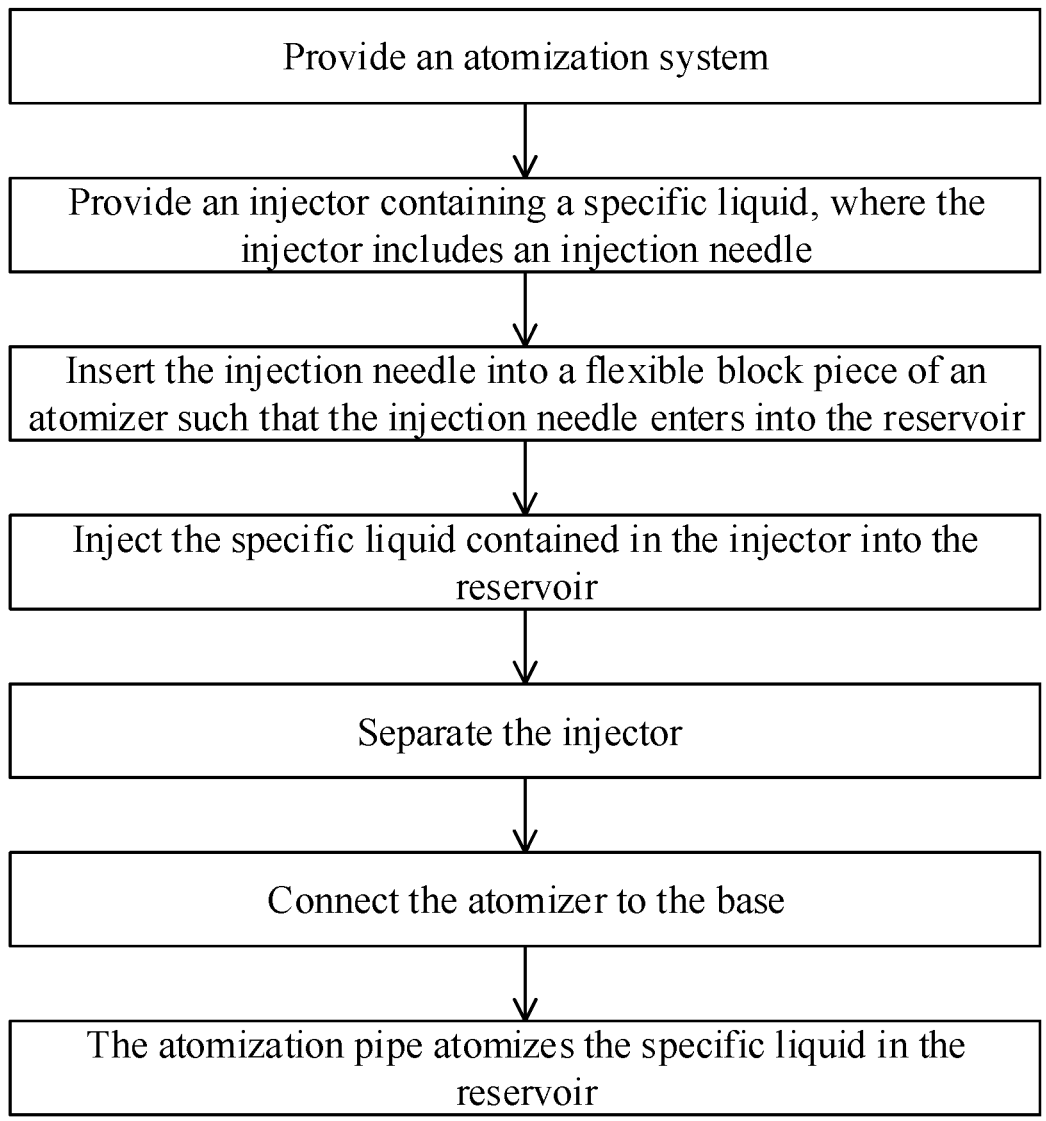
FIG. 6 is a flowchart of an operation method of the atomization system according to embodiment five of the present disclosure.

As shown in FIG. 6, an operation method of the atomization system is provided in the present disclosure and is used for operating the atomization system provided by the embodiment four. The operation method includes the steps below.

In S1, an atomization system is provided. The atomization system is, for example, but not limited to, the atomization system of embodiment four. The user may atomize the specific liquid in the reservoir 2 through the base 10 and the atomizer of the atomization system, so as to inhale the atomized medicine or smoke oil through the user's respiratory system. When it is necessary to add or refill the specific liquid in the reservoir 2, the user may inject the specific liquid into the reservoir 2 by performing the following steps.

In S2, an injector containing the specific liquid is provided, where the injector includes an injection needle. The injector may include a syringe and a syringe needle in the related art.

In S3, the injection needle is inserted into a flexible block piece 3 of an atomizer such that the injection needle extends into the reservoir 2.

In S4, the specific liquid contained in the injector is injected into the reservoir 2.

In S5, the injector is separated. When the user injects the specific liquid to be added into the reservoir 2 through the injector and the injection needle, the injector may be separated from the atomizer, and the injection needle may also be withdrawn from the flexible block piece 3. Since the flexible block piece 3 is made of flexible material, after the injection needle is withdrawn, the flexible block piece 3 will be restored to an original state without generating pinholes, so that the specific liquid in the reservoir 2 will not leak out. The user may proceed with the following steps, using the atomization system to atomize the specific liquid in the reservoir 2.

In S6, the atomizer is connected to the base 10.

In S7, the atomization pipe 1 atomizes the specific liquid in the reservoir 2. When the specific liquid in the reservoir 2 needs to be added again, the above steps S2 to S5 can be repeated, so that the atomizer can be reused.

Apparently, the above embodiments of the present disclosure are merely illustrative of the present disclosure and are not intended to limit the embodiments of the present disclosure. For those of ordinary skill in the art, alterations or modifications in other different forms can be made based on the above description. Implementations of the present disclosure cannot be and do not need to be all exhausted herein. Any modification, equivalent substitution and improvement within the spirit and principle of the present disclosure fall within the scope of the claims of the present disclosure.

What is claimed is:

1. An atomization system, comprising a base and an atomizer, wherein the atomizer is detachably connected to the base, and the atomizer comprises:
   an atomization pipe comprising an opening, wherein the opening penetrates through an outer surface of the atomization pipe;
   a reservoir disposed in the atomization pipe, wherein the opening is communicated with the reservoir; and
   a flexible block piece disposed in the opening, wherein the flexible block piece is configured to allow an injection needle to pass through the flexible block piece and enter the reservoir;
   wherein the base comprises a rod body, a coupling slot and a battery wherein the coupling slot is located at one end of the rod body, the battery is disposed in the rod body, and one end of the atomization pipe provided with the flexible block piece is detachably coupled in the coupling slot.

2. The atomization system of claim 1, wherein the flexible block piece is made of a flexible plastic material or a flexible silica gel material.

3. The atomization system of claim 1, wherein the atomizer further comprises a fixing piece, wherein the fixing piece is sealed outside the opening and is attached to the flexible block piece, and the fixing piece is provided with a through hole.

4. The atomization system of claim 1, wherein the atomizer further comprises an atomization device, wherein the atomization device is disposed in the atomization pipe and is configured to generate heat.

5. The atomization system of claim 4, wherein the atomizer further comprises a conductive contact, wherein the conductive contact is electrically connected to the atomization device.

6. The atomization system of claim 1, wherein the atomizer further comprises a nozzle, wherein the nozzle is connected to one side of the atomization pipe, wherein the atomization pipe further comprises a through cavity, and the through cavity is communicated with the reservoir and the nozzle.

7. The atomization system of claim 6, wherein the atomizer further comprises an end cap, wherein the end cap covers the nozzle.

8. The atomization system of claim 1, wherein the atomization pipe further comprises a docking portion and a body, the docking portion extends axially from the body and the docking portion is radially inward relative to the body, and the opening and the flexible block piece are located in the docking portion.

9. An operation method of an atomization system, comprising:
   providing an atomization system, wherein the atomization system comprises a base and an atomizer, wherein the atomizer is detachably connected to the base, and the atomizer comprises: an atomization pipe comprising an opening, wherein the opening penetrates through an outer surface of the atomization pipe; a reservoir disposed in the atomization pipe, wherein the opening is communicated with the reservoir; and a flexible block piece disposed in the opening, wherein the flexible block piece is configured to allow an injection needle to pass through the flexible block piece and enter the reservoir;
   providing an injector containing a specific liquid, wherein the injector comprises the injection needle;
   inserting the injection needle into the flexible block piece of the atomizer such that the injection needle enters into the reservoir;
   injecting the specific liquid contained in the injector into the reservoir;
   separating the injector;
   connecting the atomizer to the base; and
   atomizing, by the atomization pipe, the specific liquid in the reservoir;
   wherein the base comprises a rod body, a coupling slot and a battery, wherein the coupling slot is located at one end of the rod body, the battery is disposed in the rod body, and one end of the atomization pipe provided with the flexible block piece is detachably coupled in the coupling slot.

10. The operation method of an atomization system of claim 9, wherein the flexible block piece is made of a flexible plastic material or a flexible silica gel material.

* * * * *